United States Patent
Tokhtuev et al.

(10) Patent No.: US 6,916,219 B2
(45) Date of Patent: Jul. 12, 2005

(54) REMOTE SAMPLING SYSTEM

(75) Inventors: Eugene Tokhtuev, Duluth, MN (US); Anatoly Skirda, Duluth, MN (US); Viktor Slobodyan, Duluth, MN (US); Christopher Owen, Duluth, MN (US)

(73) Assignee: Apprise Technologies, Inc., Duluth, MN (US)

( * ) Notice: Subject to any disclaimer, the term of this patent is extended or adjusted under 35 U.S.C. 154(b) by 302 days.

(21) Appl. No.: 10/290,403

(22) Filed: Nov. 8, 2002

(65) Prior Publication Data

US 2003/0092393 A1 May 15, 2003

Related U.S. Application Data

(60) Provisional application No. 60/331,193, filed on Nov. 9, 2001.

(51) Int. Cl.[7] .............................................. B63B 22/20
(52) U.S. Cl. ....................................................... 441/29
(58) Field of Search ................................ 441/1, 28, 26, 441/27, 29

(56) References Cited

U.S. PATENT DOCUMENTS

| | | | | |
|---|---|---|---|---|
| 5,004,014 A | * | 4/1991 | Bender | 137/624.12 |
| 5,224,074 A | * | 6/1993 | Sullivan | 367/3 |
| 5,551,800 A | * | 9/1996 | Hobelsberger | 405/186 |
| 5,655,938 A | * | 8/1997 | Huguenin et al. | 441/29 |
| 5,816,874 A | * | 10/1998 | Juran et al. | 441/1 |

* cited by examiner

*Primary Examiner*—Stephen Avila
(74) *Attorney, Agent, or Firm*—Reed Smith LLP; Stanley P. Fisher, Esq.; Juan Carlos A. Marquez, Esq.

(57) ABSTRACT

An automated system for periodically sampling water bodies, such as lakes, and delivering the test results to a remote computer using a communication system. In particular, the system has a variable buoyancy profiler with a dynamic buoyancy compensator responding approximately linear to a water pressure created by an external water body so as to actively or passively interact with an external force or pressure thereby moving the profiler to a target depth.

49 Claims, 16 Drawing Sheets

REMOTE SAMPLING SYSTEM

This application claims the benefit of U.S. Provisional Patent Applications Ser. No. 60/331,193 filed on Nov. 9, 2001, the entire disclosures of which are incorporated herein by reference.

BACKGROUND OF THE INVENTION

1. Field of the Invention

The invention generally relates to analytical systems and methods for automated sampling and measuring of various parameters for environmental purposes, water management, process optimization and early warning system for monitoring, management and mitigation efforts. More particularly it relates to an automated system for the periodic profiling of water bodies like lakes, rivers, reservoirs and estuaries and delivering the test results to a remote computer using a communication system.

2. Description of Related Arts

The invention may be used for the remote measuring of environmental parameters using one or several autonomous stations having a deployment platform with a power supply system, controller unit and a communication system, wherein said deployment platform connected through an underwater cable to the sampling device made as a variable buoyancy profiler with a sensor package.

In the prior art, an autonomous oceanographic profiler has been developed for collecting information about water quality. U.S. Pat. No. 5,283,767 describes a profiler carrying a sensor package and changing buoyancy using a mechanical trim piston. The mechanical piston system provides near 50 $cm^3$ of profiler volume change. This profiler has no permanent connection with the base station and cannot send real time data.

Another device is the variable buoyancy ballast and flotation unit described in U.S. Pat. No. 5,655,938 or the sonobuoy according to U.S. Pat. No. 5,224,074, which use valves and compressed air to change the buoyancy of the submersible units. For extended operation the system must be recharged.

The buoyancy control system, which is described in U.S. Pat. No. 5,379,267 is also capable of being moved vertically, but this system operates by discharging measured quantities of either a heavy or light liquid. For extended operation the system also has to be recharged.

The remote sensing station that is described in U.S. Pat. No. 5,816,874 has a depth control housing with a sealed interior chamber and a pump providing water inside the interior chamber to adjust buoyancy. This system has a limited operational time and depth range because air inside of said chamber is not separated from the water therefore during pumping cycles air will be gradually dissolved in the water, which is pumping in and out. Because the air pressure inside the chamber is low and becomes even lower during operation the pump is required to overcome the external water pressure at the maximum depth. Such profiler uses electrical power with low efficiency and cannot work at a depth where water pressure is higher than the maximum pressure of the pump. A guide line for guiding the profiler described in this patent provides additional friction during profiler movements that increases power consumption and adversely effects the accuracy of the system.

The method and apparatus for controlling the depth of submergence of an underwater vehicle that is described in U.S. Pat. No. 3,675,607 works with positive buoyancy of a submerged housing but, according to the patent, it should be constant at the different depth and lower by the absolute value then negative buoyancy of the cable and a depth control body. Precise depth control is obtained by controlling the length of the cable. This method and apparatus requires constant controlling of the cable length, a large power budget, and a depth control body operating with a negative buoyancy and laying on the bottom of the water body.

The buoyancy compensators described in U.S. Pat. Nos. 3,820,348, 4,114,389, 5,551,800 need pressurized air for their operation, and all of them are designed to increase buoyancy when the buoyancy compensator moves from the water surface to the deep water.

SUMMARY OF THE INVENTION

It is an object of the present invention to increase the efficiency of the analytical system; methods for automated sampling and measuring of various parameters at discrete depths and prolong the time of operation without human interference.

It is another object of the present invention to increase the depth range for the profiler and to improve the power efficiency of the overall operational methods.

It is a further object of the present invention to make the buoyancy of the profiler self-adjustable to outside pressure of different depths and provide a means to move the profiler from the water surface to maximum depth using low force drives.

Other objects and advantages of the present invention may be seen from the following detailed description:

The present invention, remote sampling system, consists of a base station with a computer or microcontroller, a telecommunication device and a one or several autonomous remote sampling stations. In one of the embodiments the remote sampling station comprises a specially designed buoy that is anchored at a selected location where a suite of water quality parameters and meteorological, as well as other critical light, climate and water quality and physical characteristics will be measured.

The methods of buoyancy modification which are described in the present invention include using dynamic buoyancy compensators which are constructed as a single or set of sealed compartments with sealed pressurized air chambers inside or as sealed cylinders with pistons supported by springs or as sylphons (i.e., devices similar to bellows as describe in U.S. Pat. No. 6,374,475) with spring members inside. The pressures inside the pressurized air chambers or counter forces of spring members inside the sealed cylinders or sylphons are adjusted to linearize their response to the outside pressure.

The dynamic buoyancy compensator may be built as an active device when water is pumping in and out or as a passive device when the profiler has been moving to the target depth with an open input of the dynamic buoyancy compensator using an external force, for example, with the assistance of a motor-driven water propeller. For the passive device, water is forced in or out by the difference in pressure inside and outside of the passive dynamic buoyancy compensator. To improve accuracy, in some embodiment the dynamic buoyancy compensator may work in passive mode when approaching the target depth and in active mode when close to the target point.

At any specific depth the dynamic buoyancy compensator changes its buoyancy close to a linear function of depth, wherein the combination of the buoyancy of the profiler and the hanging cable results in neutral buoyancy, however, with the dynamic buoyancy compensators closed any shifts from this position up or down will generate force tending to return this system to equilibrium position.

Deviations between the pressure inside and outside of the dynamic buoyancy compensator are small at any depth, which allows the profiler to operate with low-pressure pump alone or in consort with a low power propeller drive. During movements the said dynamic buoyancy compensator changes its buoyancy corresponding to current depth and at the target depth it may be disconnected from the water body. After the dynamic buoyancy compensator is disconnected the profiler stays at the target depth until the next order for changing depth.

The profiler unit undertakes a series of steps to maneuver vertically in a column of water. These steps include: 1). The controller unit reads depth data from the depth sensor. 2). The controller unit compares current depth and desired programmed depth (target depth). 3). The controller unit modifies buoyancy of profiler by the methods described in the following claims, where depth is constantly monitored and velocity of profiler calculated to achieve target depth in the shortest possible time or with the lowest possible expenditure of energy. 4). When current depth equals target depth, the controller unit acquires data.

BRIEF DESCRIPTION OF THE DRAWINGS

The foregoing and additional features and characteristics of the present invention will become more apparent from the following detailed description considered with reference to the accompanying drawings in which like reference numerals designate like elements and wherein.

DETAILED DESCRIPTION OF THE PREFERRED EMBODIMENTS

The remote sampling system, according to the present invention, includes a base station with computer or micro controller, a telecommunication device and one or several autonomous remote sampling stations. Three embodiments are shown in FIG. 1A, FIG. 1B and FIG. 1C.

Figure 1A:
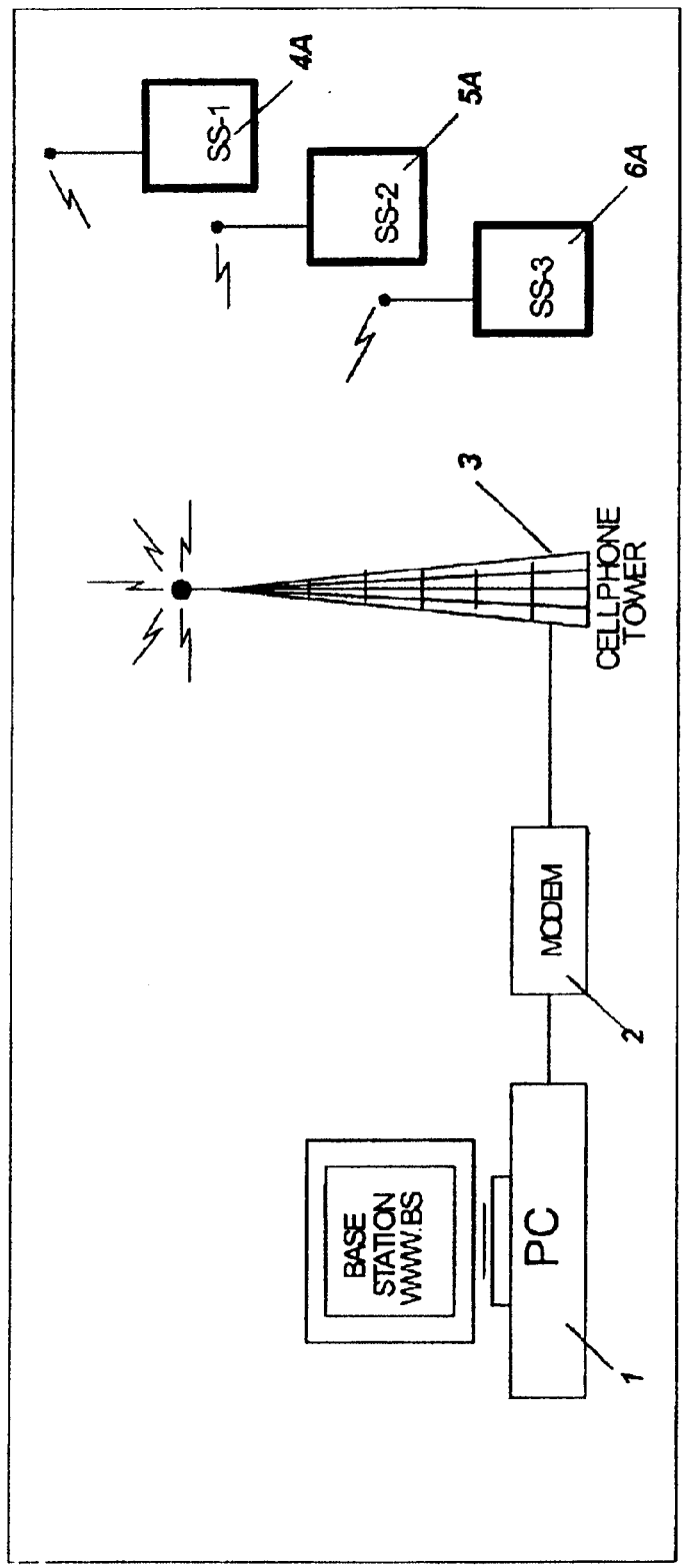
FIG. 1A is a schematic drawing of a remote sampling system with a base station, landline modem, cellular communication station and multiple remote sampling stations

The remote sampling station shown in FIG. 1A includes a base station with a personal computer 1 and a landline modem 2. The landline modem 2 through a cellular communication station 3 receives information from remote sampling stations 4A, 5A, 6A which are equipped with cellular modems.

Figure 1B:
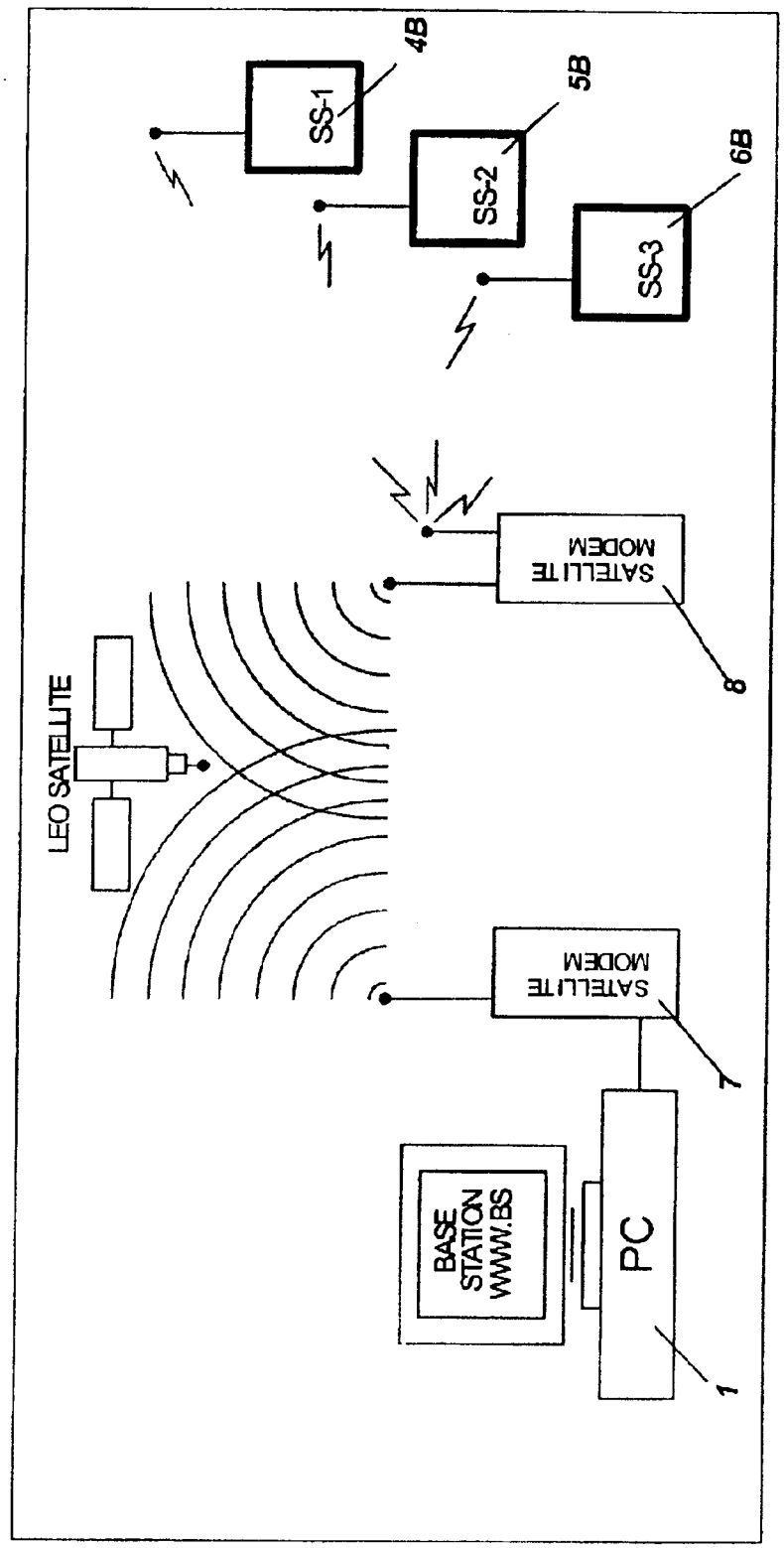
FIG. 1B is a schematic drawing of a remote sampling system with a base station, satellite modems and multiple remote sampling stations

The remote sampling station shown at the FIG. 1B includes a base station with a personal computer 1 and a satellite modem 7. The satellite modem 7 through the LEO (Low Earth Orbit) or other satellite system communicates with another satellite modem 8, which receives information from remote sampling stations 4B, 5B, and 6B. The satellite modem 8 and the remote sampling stations 4B, 5B and 6B are equipped with radio modems for exchanging information.

Figure 1C:
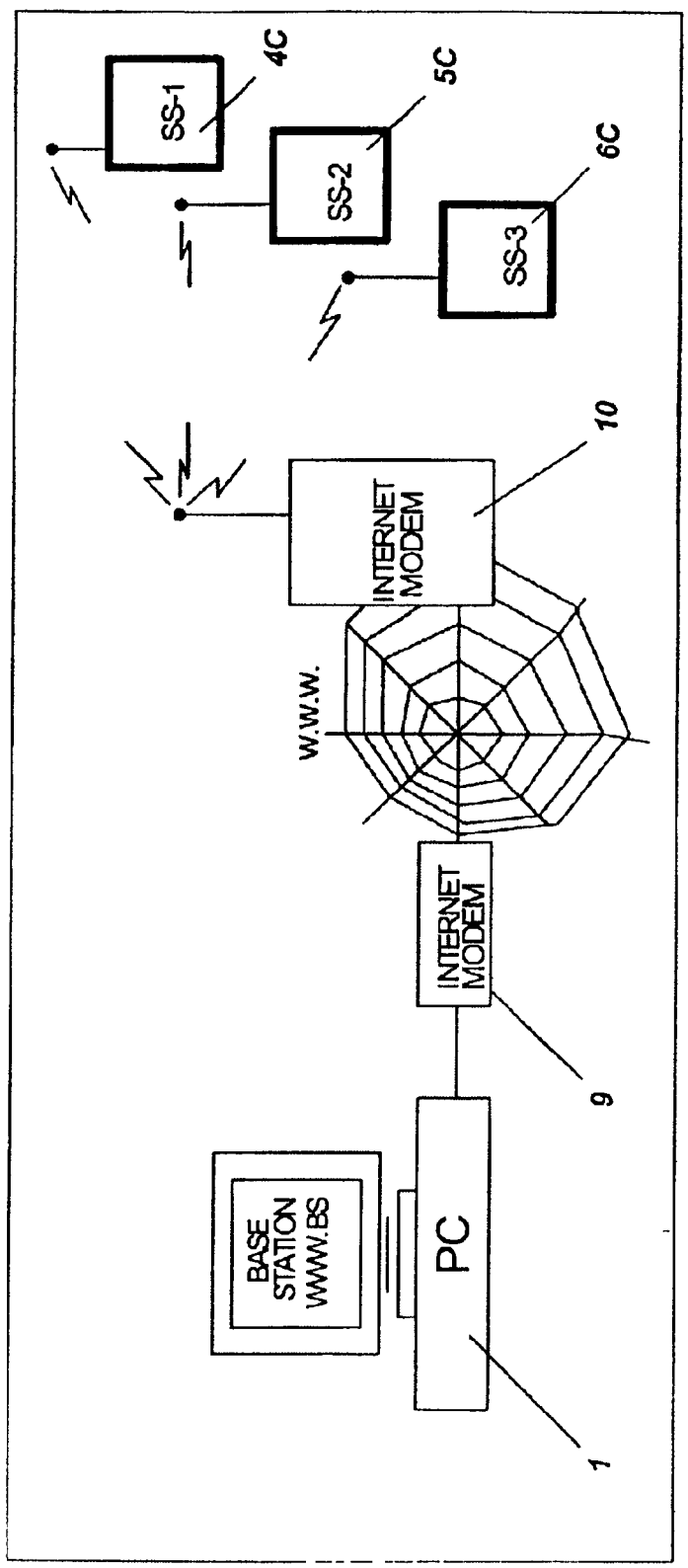
FIG. 1C is a schematic drawing of a remote sampling system with base station, Internet modems and multiple remote sampling stations.

The remote sampling station shown at the FIG. 1C includes a base station with a personal computer 1 and an Internet modem 9. The Internet modem 9 communicates through the World Wide Web with another Internet modem 10, which receives information from remote sampling stations 4C, 5C, and 6C. The Internet modem 10 and the remote sampling stations 4C, 5C, and 6C are equipped with 900 MHz modems or other telecommunication devices for exchanging information.

Connected to the buoy, the variable buoyancy profiler with one or several sensing devices collects different parameters at preprogrammed depths along the water column. Data from the sensing devices attached to the profiler is transmitted to the controller unit through an underwater cable. The controller unit uses data from a sensor included in the sensing device or data from an independent depth sensor mounted on the profiler to control the buoyancy of profiler, which controls the profiler movements in the body of water. Changing of buoyancy controls the profiler movement in one embodiment. In other embodiments, the profiler moves in water by traction forces of a propeller. The buoyancy of the profiler has the maximal value when near the water surface. The overall profiler buoyancy is positive and is equilibrated to neutral buoyancy by the negative buoyancy of the cable length looped under the profiler. At the maximum depth, the profiler has approximately zero buoyancy. At any depth, the profiler may be in a stable position if its positive buoyancy at this depth is compensated by the loop of cable under the profiler and its associated negative buoyancy. The portion of the cable from the profiler to the lowest point at the cable (turning point) is carried by the profiler, and buoy supports the remaining cable between the lowest point at the cable (turning point) and the buoy floating on the surface of the water.

Figure 2:
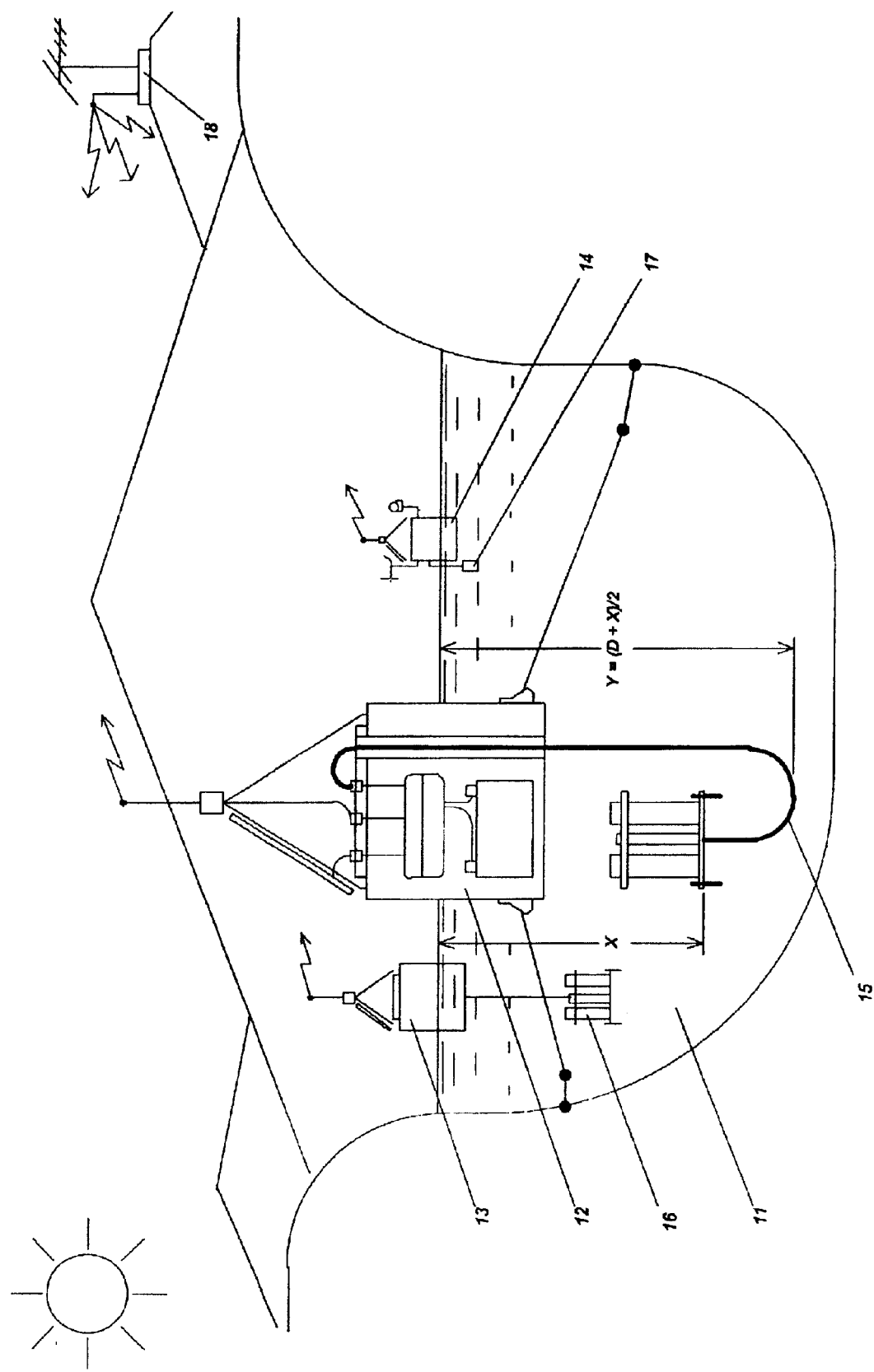
FIG. 2 is a schematic drawing of multiple remote sample stations in the remote sampling system for automated water analysis.
Figure 3A:
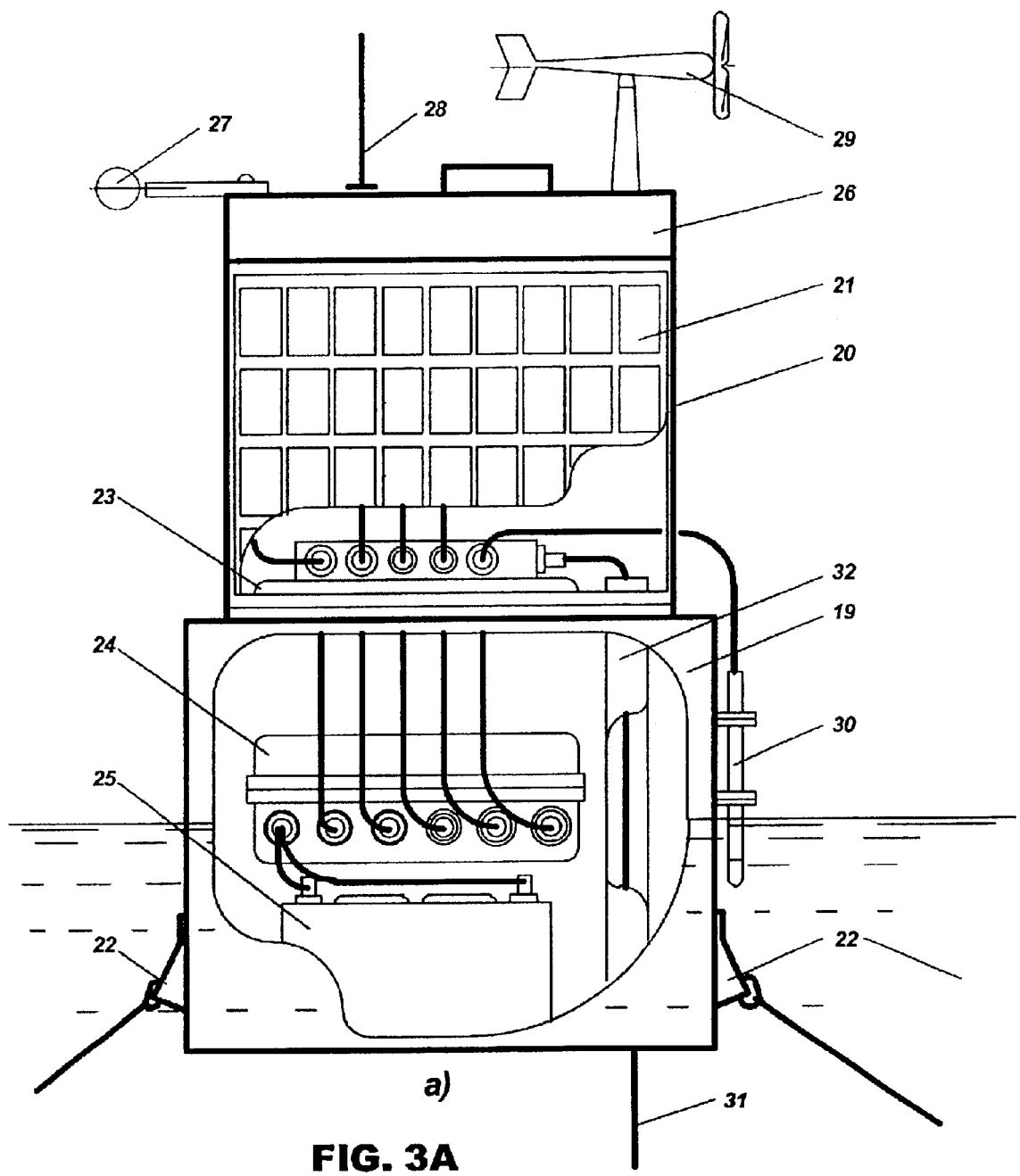
FIG. 3 is a schematic drawing of the remote sampling station.
Figure 3B:
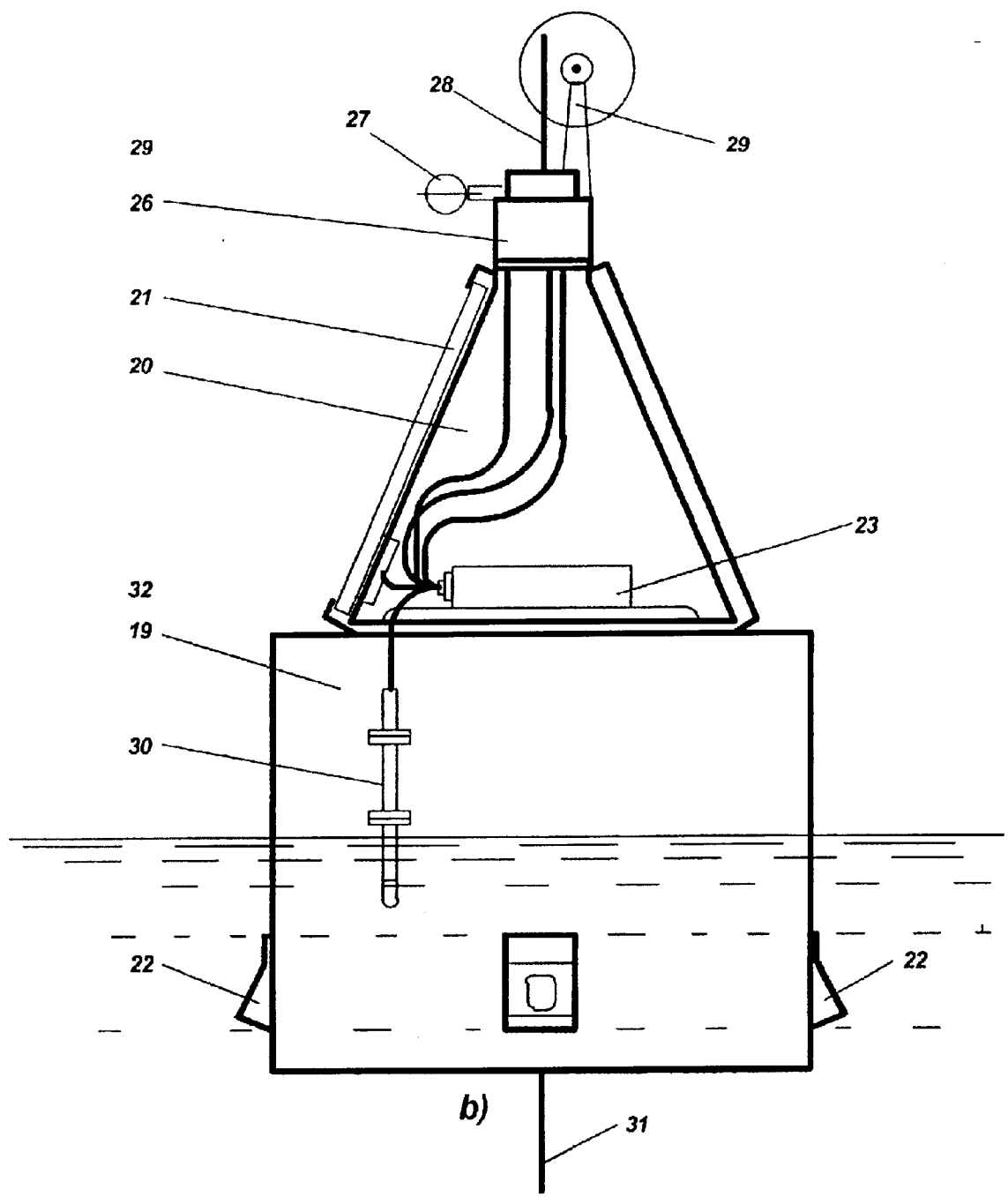

The remote sampling stations for automated water analysis are shown in FIG. 2. It shows a body of water 11 with remote sampling stations 12, 13, 14. The remote sampling station 12 has a variable buoyancy profiler 15 with sensing devices. The variable buoyancy profiler is linked to the deployment platform with an underwater cable with a total length D. When the profiler is set at the depth X, the distance Y from the surface of water to the turning point of the underwater cable equals approximately to $Y=(D+X)/2$ as shown in FIG. 2. Another remote sampling station 13 has a fixed-depth sensing device 16. The remote sampling station 14 has at least one analyzer 17. The remote sampling stations 12, 13, 14 are equipped with communication means to exchange information via a relay link 18 which expedites data to a base station. FIG. 3A and FIG. 3B show a front view and a side view of a deployment platform of the remote sampling station 12. The deployment platform includes a watertight case 19 and a support tower 20. The support tower 20 has a solar panel 21 attached to its side. The watertight case 19 has four cable clamps 22 for attaching underwater cables when the unit is deployed. The watertight case 19 is covered with a hatch cover 23 to protect a controller unit 24 and a battery 25 placed inside of the watertight case. An emergency buoy 26 at the top of the support tower 20 helps to return the deployment platform to the correct position if it is flipped by waves upside down. When the emergency buoy 26 is placed under the deployment platform in water, its buoyancy makes this position unstable. Any small tilt will rotates the deployment platform to the horizontal position such that the emergency buoy 26 and the platform are rotated to their normal vertical orientation.

The deployment platform is attached with sensors and devices such as a radiation sensor 27, an antenna 28, a meteorological station 29, a surface water thermometer 30, etc. If the deployment platform is equipped with an underwater sensing device, it has an underwater cable 31 directed through a sealed cable shaft 32.

The remote sampling stations in some embodiments include not only fixed depth sensing devices for measuring water parameters at the constant depth but profiling devices for delivering sensor packages to the different depth in the body of water. The preferable profiling device is a variable buoyancy profiler according to the present invention.

The remote sampling station has the following capabilities: 1) Stores data from all attached sensors (underwater sensors, meteorological and positioning sensors). 2) Stores voltage levels from the power supply. 3) Archives user log files of all system activities (data, connection attempts, users activities, etc.). 4) Transmits the stored data to a land base station via cellular telephone communication or other bi-directional telemetry device. 5) Has the capacity of both remote and manual programmability (remotely from the land station or "in situ" by field personnel) to acquire data at pre-selected times and depths. 6) Has the ability to call the base station (or any other phone number like a beeper) when a sensor parameter (GPS data, voltage, or other) is beyond a preprogrammed range (i.e. variable trigger point automated communication protocol). 7) Allows full operation from a field operator with a portable computer and proper software and cable connectors. 8) Has several security password-protected levels of authorization for full operation and programming or data downloading only accessible through the propriety operational software. The remote sampling station receives electrical power from batteries and has one or multiple solar panels to charge said batteries.

Figure 4:
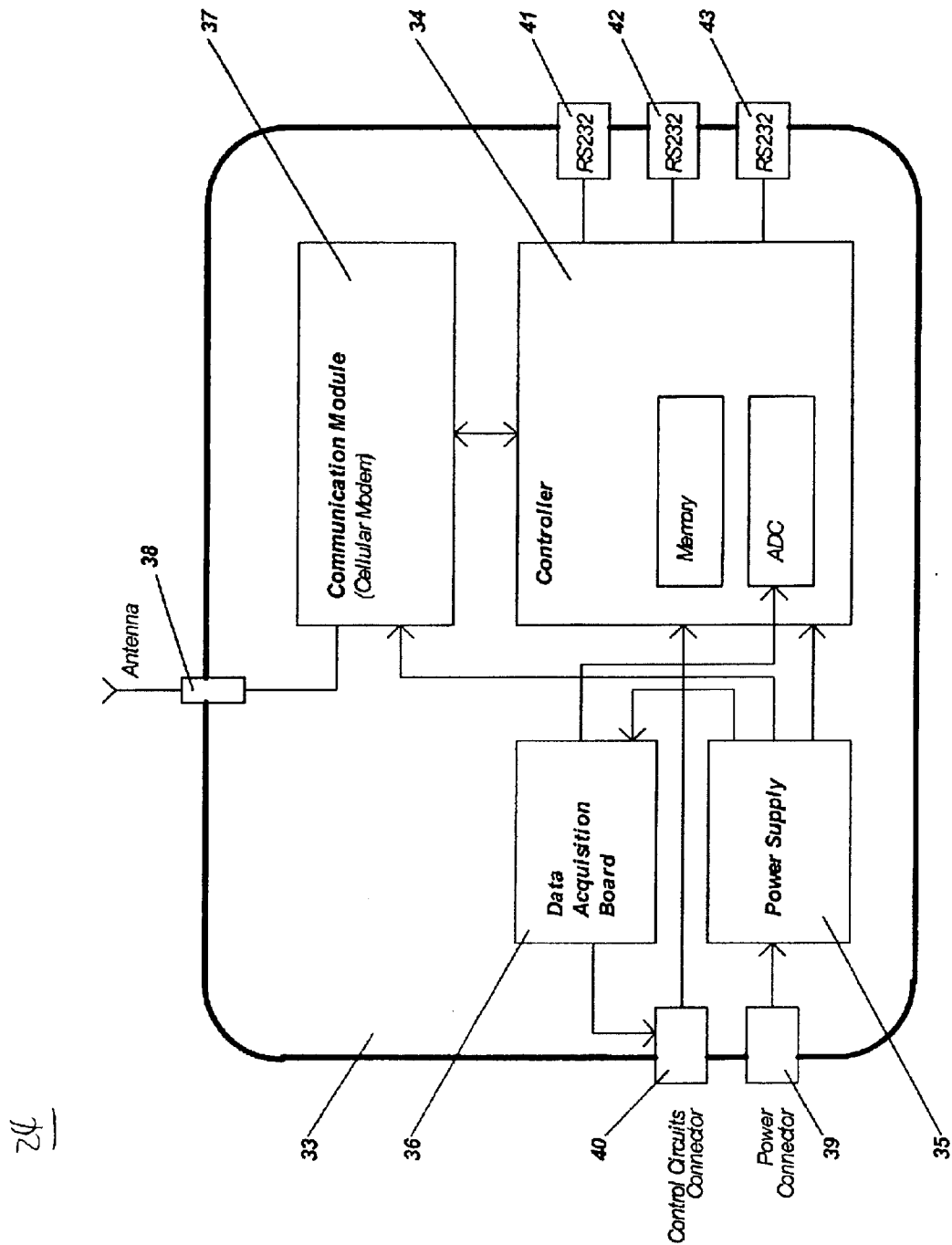
FIG. 4 is a schematic drawing of the controller unit with the cellular modem.

FIG. 4 shows the controller unit 24. It has a watertight case 33 which includes a controller 34, a power supply 35, a data acquisition board 36, a communication module 37 (such as a cellular modem), an antenna connector 38, a power connector 39, a control circuits connector 40 and connectors of communication ports 41, 42, 43. The preferred embodiment for the variable buoyancy profiler 15 is shown at the FIG. 5. The variable buoyancy profiler 15 has a sealed control compartment 44 with a control circuit 45. The control circuit 45 is connected to an underwater cable connector 46 and to the connector of the sensing device 47. The variable buoyancy profiler 15 has a first protective cylinder 48 for accommodating the sealed control compartment 44 and a second protective cylinder 49 for accommodating a variable buoyancy compartment, which includes rubber chambers 50, valves 51 for each of said rubber chambers, and a cylinder valve 52 for the second protective cylinder. Each of the valves 51 open a corresponding rubber chamber to let in air then close before the deployment of the profiler. Each of the rubber chambers 50 is covered with a rigid protective shell 50a which supports the respective rubber chamber containing air but allows water pressure to pressurize the rubber chamber individually. The first and second protective cylinders are sealed with the O-Rings 53. The O-Rings 53 are compressed in grooves on the base plate 54 with screws 55. Several coil-type thread inserts in the cylinders are pulled to the base plate 54 with screws 54. Inside of the sealed control compartment 44, there is input water tubing 56, which is connected to a water filter 57 for cleaning water for a reversible water pump 58. The reversible water pump 58 through electrical valves 59 is connected to a flow meter 60 and output water tubing 61. The output water tubing 61 is connected to a compensating tubing 62 inside the second protective cylinder 49 to equalize the water pressure inside of the cylinder with the external water pressure at the corresponding depth. A volume between an inner wall of the rigid sealed compartment and an outer surface of each sealed elastic chamber 50 is filled with water and connected to the external water body through an electrical valve 52, which is a two-way valve. Optimal pressures in the rubber chambers 50 and their volume vary according to the maximum depth of the profiler.

The connectors 46 and 47 at the base plate 54 are connected to a underwater cable 63 and a sensing device 64. The variable buoyancy profiler 15 has weight holders 65 to hold balancing weights 66, legs 67 and sensor holders 68 with a clamp thereby attaching different sensing devices. In another embodiment, the control circuit 45 includes an adjustable voltage reference for stabilizing pump current and thereof a maximum output pressure at the appointed level, and a semiconductor switch to change the direction of the pump current. The adjustable voltage reference could be made as a modulated voltage reference or as a programmable voltage reference to change periodically the pump current and thereof the maximum output pressure. With a programmable voltage reference, the pump current could be set high at the beginning of depth position and low when profiler approaches to a target depth to increase accuracy of profiler positioning and eliminate oscillating while approaching to the target depth. In some embodiments, the control circuit 45 uses the voltage output of the flow meter 60 to stabilize the water flow from the pump. The flow meter 60 is built with a differential pressure sensor connected to the section of the input or output tubing. In another embodiment, the output of the flow meter is permanently connected to the controller unit 24. Before the profiler 15 is moved to the next depth, the controller 34 calculates what volume of water to be pumped in or out and then integrates data of the flow meter to stop the pump when this volume is pumped in or out. The sealed rubber chambers 50 are pressurized to a different internal pressure therein such that their total pressure response close to linear to the water has been pumping in. Such an operation mode consumes less power and brings the profiler 15 to the target depth without oscillations.

Figure 6:
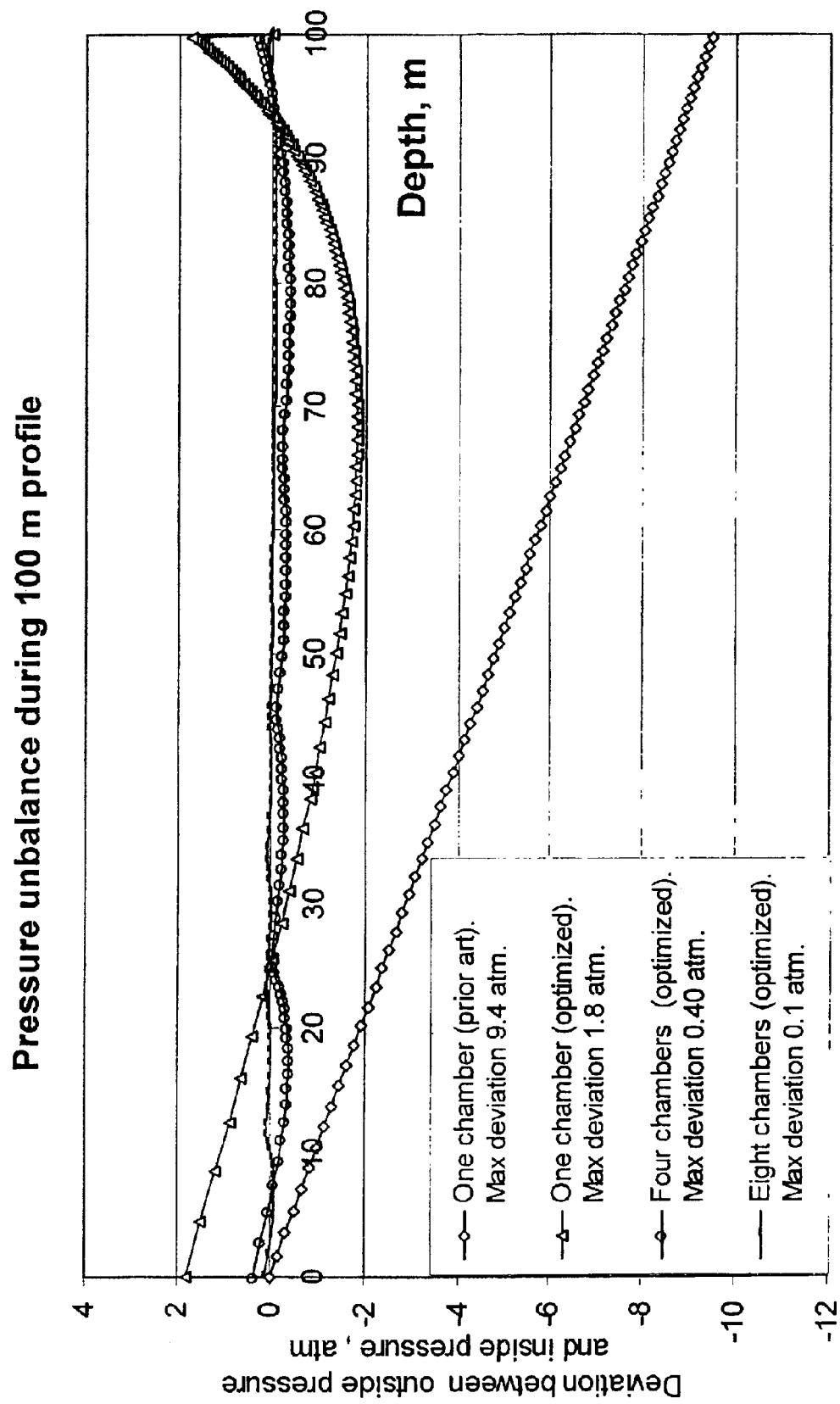
FIG. 6 is a graph showing response of dynamic buoyancy compensators to the outside pressure for the depth from 0 to 100 meters.

FIG. 6 shows deviations between the outside pressure and the inside pressure during 100 m profile for the prior art design and for several variants of the dynamic buoyancy compensator made according to the present invention. According to the prior art design, the volume of the air chamber, which creates positive buoyancy and air pressure inside of said air chamber, is not optimized. Pumping water inside of the air chamber can not greatly change the pressure inside such that the deviation between the outside and inside pressure limits the maximum depth that can be reached. At the 100 m depth, the maximum deviation in pressure is near 9.4 atm in the prior art, which takes a high pressure pump (up to 10 atm) with a big power consumption. On the other hand, the present invention with one rubber chamber provides a maximum deviation only at 1.8 atm (four, eight or ten rubber chambers provide a maximum deviation at 0.40 atm, 0.1 atm, 0.08 atm respectively).

According to the present invention, the buoyancy of the profiler is separated into two parts. The first part is static buoyancy, which is designed to compensate the weight of the profiler and all sensing devices attached to it. The second part is the dynamic buoyancy performed by a dynamic buoyancy compensator, which compensates cable weight when the profiler is near the water surface and controls the position of profiler in the water body. FIG. 6 shows an optimized dynamic buoyancy compensator with one chamber. At zero depth, the chamber contains air pressurized to the 2.8 atm and has the deviation from the atmospheric pressure 1.8 atm. To move the profiler from the water surface (zero depth) to the maximum depth, the water should be pumped inside of the dynamic buoyancy compensator, the total weight of the pumped water equals to the half of the total negative buoyancy of the maximum depth 100 m of the inside pressure. For one such chamber, the pressure inside of the dynamic buoyancy compensator will be close to 11.8 atm. But in the 100 m profiles, the pressure deviation does not exceed 1.8 atm. It allows the use of a low power water pump (with a maximum pressure of 2 or 3 atm) to send the profiler to a 100 m depth. Using a dynamic buoyancy compensator with more than one chamber allows more accurate pressure compensation. The four-chamber compensator makes the deviation not more than 0.4 atm. The eight-chamber compensator has a deviation of not more than 0.1 atm.

Figure 8:
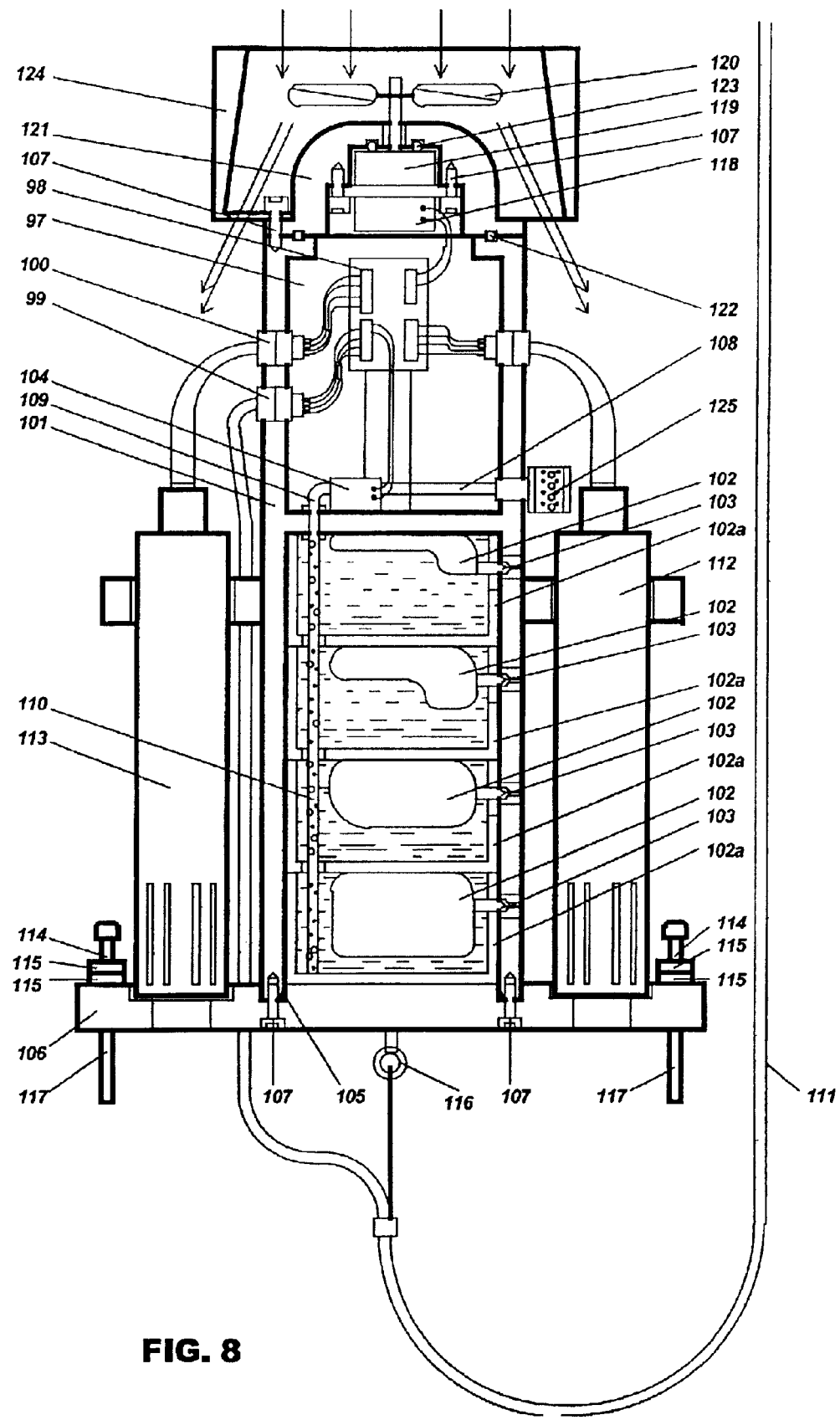
FIG. 8 is a schematic drawing of the variable buoyancy profiler with a propeller drive.

Two examples are provided to explain the volume and air pressure within each of the rubber chambers 50. In the dynamic buoyancy compensator for 100 meters with 4 chambers, there is a maximum deviation of 0.40 atm between the internal pressure and the external pressure of the compensator, if each chamber has same volume of air equal to 0.425 of the volume of water needed to send the profiler to its maximum depth (100 meters). The rubber chambers 50 (from top to bottom) have the absolute pressures of 1.39 atm, 3.50 atm, 5.70 atm, and 8.10 atm, respectively (FIG. 8). In the dynamic buoyancy compensator for 100 meters with 8 chambers, there is a maximum deviation of 0.10 atm between the internal pressure and the external pressure of the compensator, if the first top chamber has a volume of air equal 0.22 and the other seven chambers have a volume of air equal 0.24 of the volume of water needed to send the profiler to its maximum depth (100 meters). The rubber chambers 50 (from top to bottom) have the absolute pressures of 1.10 atm in the first chamber, and 2.20 atm, 3.40 atm, 4.60 atm, 5.80 atm, 7.00 atm, 8.20 atm, and 9.40 atm in the other seven chambers, respectively.

Figure 7:
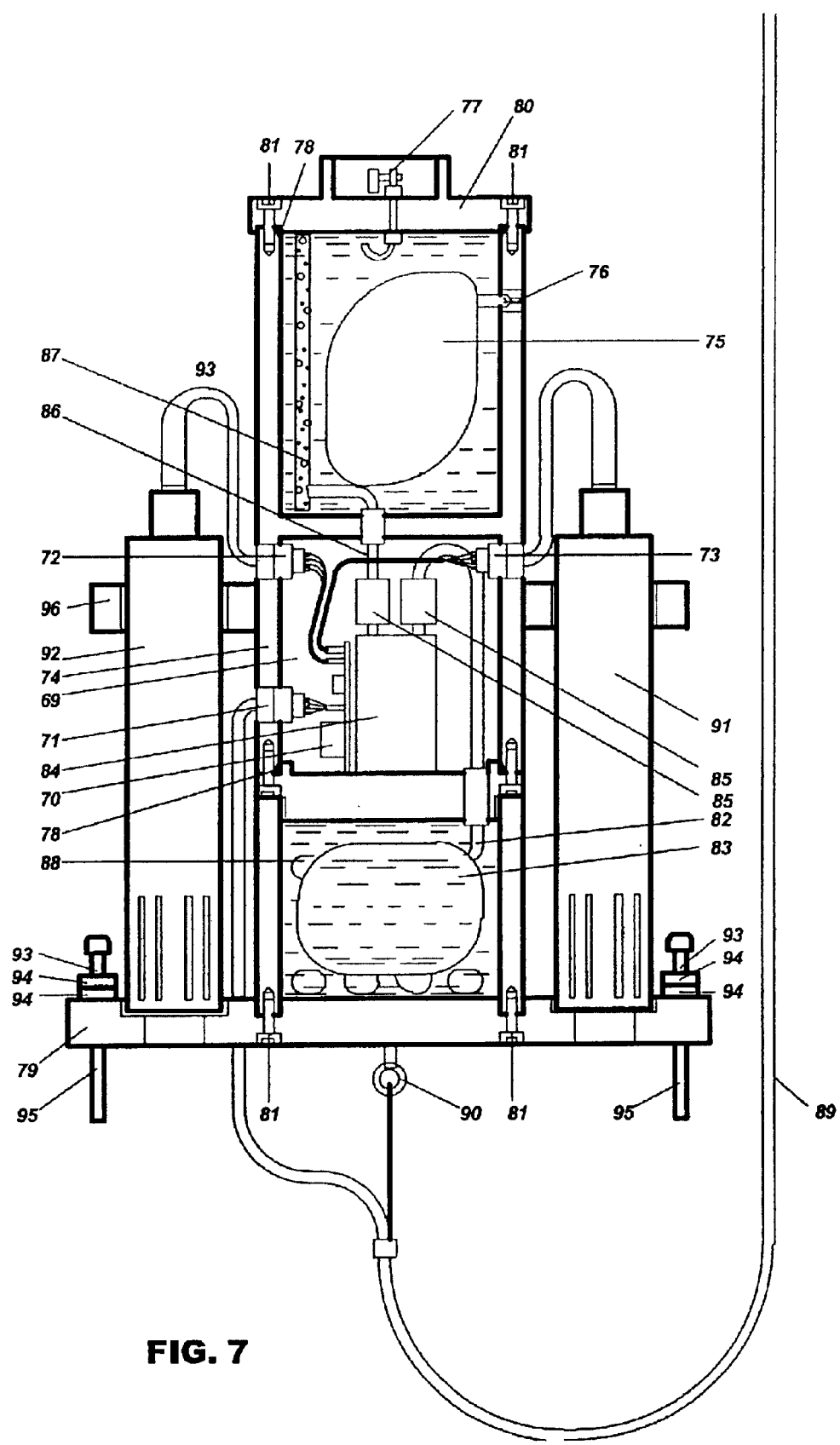
FIG. 7 is a schematic drawing of the variable buoyancy profiler with a closed water pumping system.

A preferred embodiment for a variable buoyancy profiler with closed water pumping system is shown in FIG. 7. The variable buoyancy profiler has a sealed control compartment 69 a control circuit 70. The control circuit 70 is connected to an underwater cable connector 71 and to the connectors for sensing devices 72, 73. The variable buoyancy profiler has a protective cylinder 74 for the sealed control compartment 69, which includes a rubber chamber 75, a valve 76 and a cylinder valve 77. The protective cylinder is sealed with O-Rings 78 with a top plate 80. Inside of the sealed control compartment 69, there is input water tubing 82 connected to the reversible water pump 84. The reversible water pump 84 through an electrical valve 85 is connected to the rubber chamber 83 located in an unsealed compartment 88 for increasing the operational period without the human intervention (to be explained later). The base plate 79 is connected with the unsealed compartment 88 by screws 81. The output water tubing 86 is connected to a compensating tubing 87 inside the second protective cylinder to equalize the pressure inside of the cylinder. The connectors 71, 72 and 73 are connected to the underwater cable 89 and sensing devices 91, 92. The cable clamp 90 holds the underwater cable 89. The variable buoyancy profiler has weight holders 93 to hold balancing weights 94, legs 95 and sensor holders 96 with a clamp for attaching different sensing devices.

FIG. 8 shows a variable buoyancy profiler with a propeller. The variable buoyancy profiler has a sealed control compartment 97 and a control circuit 98. The control circuit 98 is connected to an underwater cable connector 99 and to a connector for sensing devices 100. The variable buoyancy profiler has protective cylinder 101 for accommodating the sealed control compartment 97 and a variable buoyancy compartment having rubber chambers 102, rigid protective shells 102a and valves 103 for each of said rubber chambers. The protective cylinder is sealed with the O-Rings 105, 122 and 123. The said O-Rings are compressed by screws 107 (not all screws are shown). Inside of the sealed control compartment, there is input water tubing 108, which is connected to the water filter 125 through the electrical valve 104. The output water tubing 109 is connected to the compensating tubing 110 inside the variable buoyancy compartment to equalize the pressure inside of it. The connectors 99 and 100 on the protective cylinder 101 are connected to the underwater cable 111 and sensing devices 112, 113. The variable buoyancy profiler has weight holders 114 to hold balancing weights 115, legs 117, and a cable holder with cable clamp 116. The electrical motor 118 is situated under the cowl 121 with a magnetic drive 119 and a propeller 120. The propeller 120 produce force to move profiler up or down. It works at any depth and together with the dynamic buoyancy compensator allows to extend depth range of the profiler and reduce power consumption. The propellers available at http://cavity.ce.utexas.edu/~kinnas/uti99/uti99.html can be used in the invention. The profiler has guiding ring 124 for propeller protection.

Figure 9:
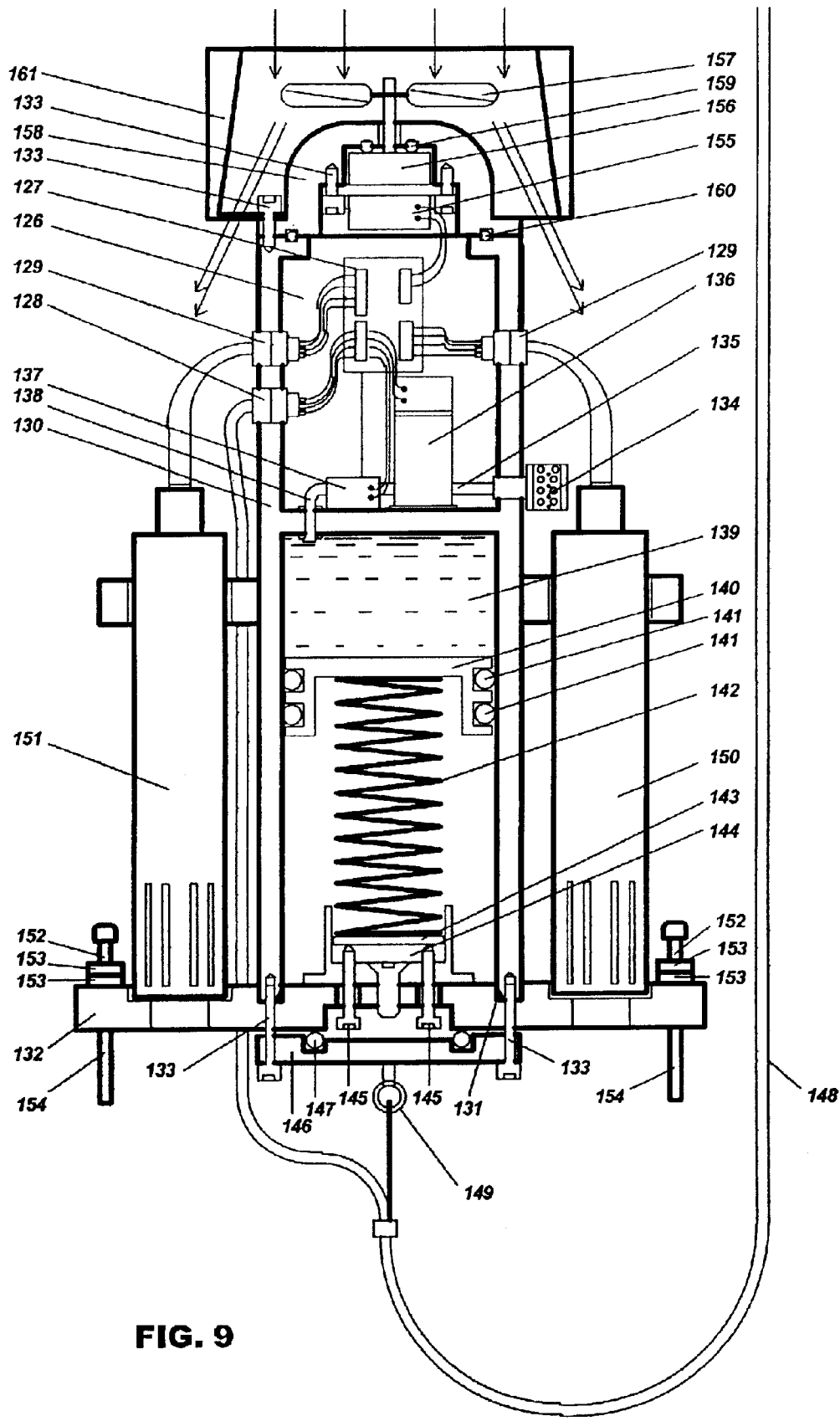
FIG. 9 is a schematic drawing of the variable buoyancy profiler with a piston dynamic buoyancy compensator.

FIG. 9 shows a variable buoyancy profiler with the piston buoyancy compensator. The variable buoyancy profiler has a sealed control compartment 126 with a control circuit 127. The control circuit 127 is connected to an underwater cable connector 128 and to a connector 129 for sensing devices 150, 151. The variable buoyancy profiler has a protective cylinder 130 for accommodating the sealed control compartment 126 and a sealed cylinder 139, which includes a moveable piston 140 with O-Rings 141, a spring member 142, a support 143, a holder 144, and adjusting screws 145. The protective cylinder 130 is sealed with the O-Rings 131, 147, 159 and 160. The O-Rings are compressed with screws 133 (not all screws are shown). Inside of the sealed control compartment, there is input water tubing 135, which is connected to a water filter 134 through a reversible water pump 136. The output water tubing 138 is connected to the sealed cylinder 139 through the valve 137. A volume between an inner wall of the sealed rigid compartment 126 and an outer surface of said piston 140 is filled with water and connected to the external water body through the electrical valve 137. The variable buoyancy profiler has weight holders 152 to hold balancing weights 153, legs 154 and a cable holder with cable clamp 149. The electrical motor 155 is situated under the cowl 158 with a magnetic drive 156 and a propeller 157. The profiler has a guiding ring 161 for propeller protection.

Figure 10:
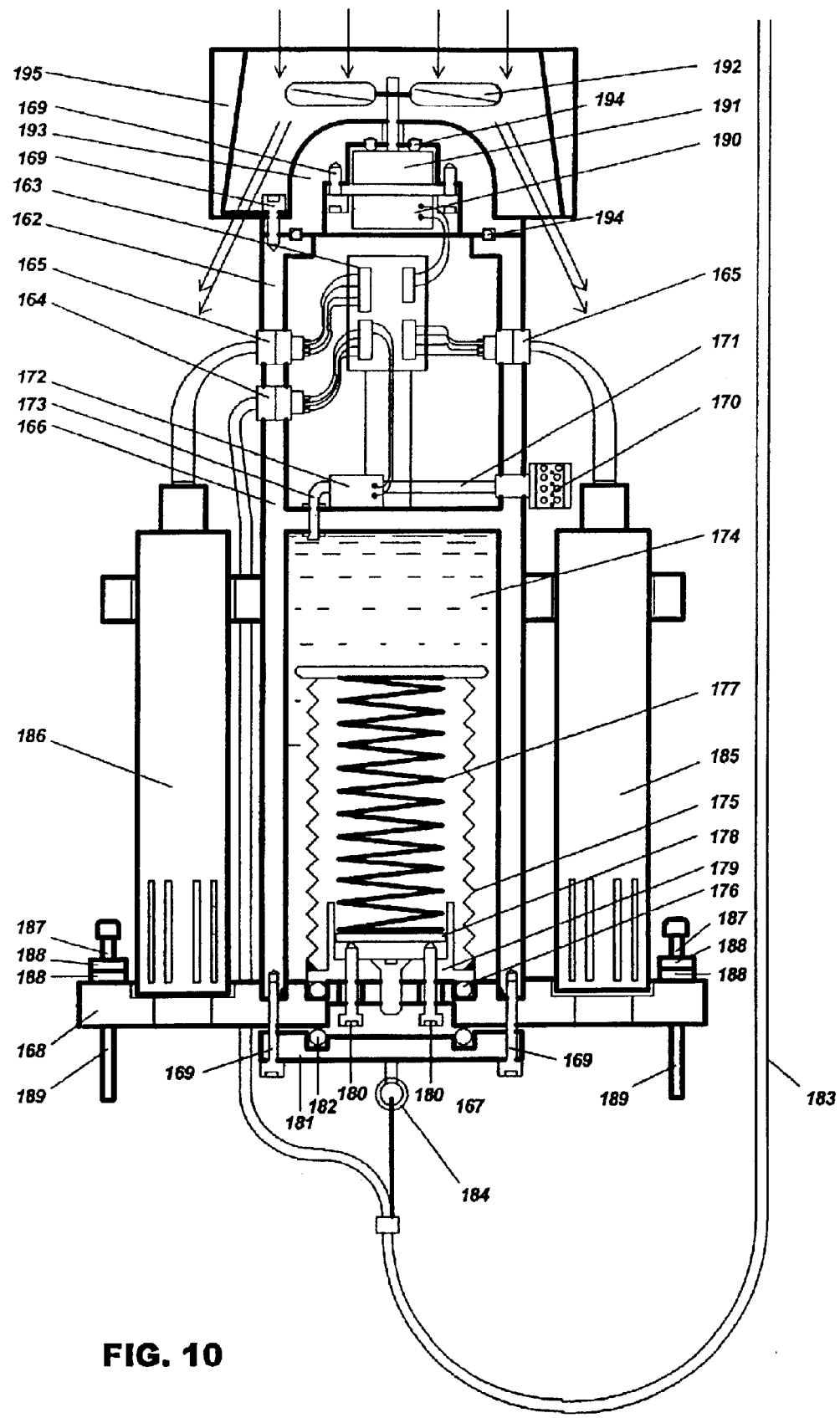
FIG. 10 is a schematic drawing of the variable buoyancy profiler with a sylphon dynamic buoyancy compensator.

FIG. 10 shows a variable buoyancy profiler with the sylphon buoyancy compensator. The variable buoyancy profiler has a sealed control compartment 162 with a control circuit 163. The control circuit 163 is connected to an underwater cable connector 164 and to a connector 165 for sensing devices 185, 186. The variable buoyancy profiler has a protective cylinder 166 for accommodating the sealed control compartment 162 and a sealed cylinder 174, which includes a sylphon 175 with an O-Ring 176, a spring member 177, a support 178, a holder 179, and adjusting screws 180. The protective cylinder 166 is sealed with the O-Rings 182 and 194. The O-Rings are compressed with screws 169(not all screws are shown). Inside of the sealed control compartment, there is input water tubing 171, which is connected to a water filter. An output water tubing 173 is connected to the sealed cylinder 174 through an electrical valve 172. A volume between an inner wall of the sealed compartment 162 and an outer surface of the sylphon 175 is filled with water and connected to water body through the electrical valve 172. The variable buoyancy profiler has weight holders 187 to hold balancing weights 188, legs 189 and a cable holder with cable clamp 184. A sealed protection cover 181 with an O-ring 182 is provided at the bottom of the profiler. An electrical motor 190 is situated under the cowl 193 with a magnetic drive 191 and a propeller 192. The profiler has a guiding ring 195 for propeller protection.

Figure 11:
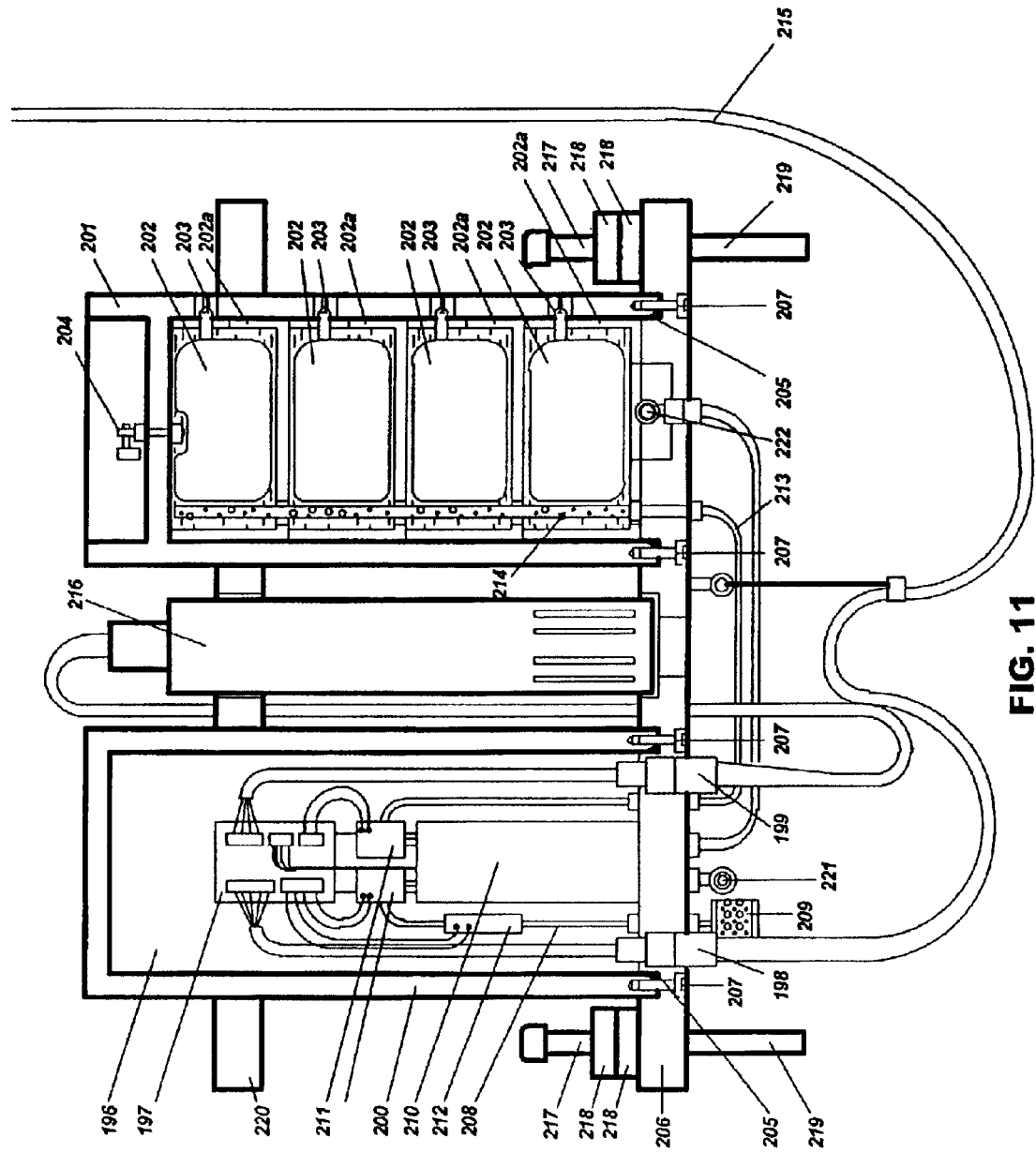
FIG. 11 is a schematic drawing of the variable buoyancy profiler with a depth sensor and a pressure sensor.

FIG. 11 shows a variable buoyancy profiler with a depth sensor and a pressure sensor. The variable buoyancy profiler has a sealed control compartment 196 with a control circuit 197. The control circuit 197 is connected to an underwater cable connector 198 and to the connector for a sensing device 199. The variable buoyancy profiler has a first protective cylinder 200 for accommodating the sealed control compartment 196 and a second protective cylinder 201 for accommodating a variable buoyancy compartment, which includes rubber chambers 202, rigid protective shells 202a and valves 203 for each of the rubber chambers, and a cylinder valve 204 on the second protective cylinder. The first and second protective cylinders are sealed with O-Rings 205. The O-Rings are compressed in grooves on the base plate 206 with screws 207. Inside of the sealed control compartment, there is input water tubing 208, which is connected to a water filter 209 for cleaning water to a reversible water pump 210. The reversible water pump 210 is connected through electrical valves 211 to the flow meter 212 and output water tubing 213. The output water tubing 213 is connected to the compensating tubing 214 inside the second protective cylinder 196 to equalize the pressure inside of the cylinder. The connectors 198 and 199 the base plate are connected to the underwater cable 215 and a sensing device 216. The variable buoyancy profiler has weight holders 217 to hold balancing weights 218, legs 219 and sensor holders 220 with a clamp for attaching different sensing devices. The variable buoyancy profiler has a depth sensor 221 and a pressure sensor 222. As such, the profiler provides a positive static buoyancy to compensate for the negative buoyancy of the sensing devices.

The present invention provides new methods for controlling the depth of the profiler in a body of water. The main property of the dynamic buoyancy compensator is to change its buoyancy in an approximate linear fashion in response to the changing of an external pressure (which comes from outside of the profiler). This allows to passively control the depth of the profiler using an external force (which comes from outside of the dynamic buoyancy compensator), such as a water propeller, to bring the profiler to a target depth. During the moving of the profiler to the target depth, the dynamic buoyancy compensator is connected to the body of water thereby exposing the system to the external water pressure. The profiler is then maintained at the depth by the propelling force for a period of time to equalize an internal pressure of the dynamic buoyancy compensator with the external water pressure at the depth. Subsequently, the propeller is shut off and the dynamic buoyancy compensator is disconnected from the body of water With the dynamic buoyancy compensators being closed, any shifts from this position up or down will generate force tending to return this system to the equilibrium position.

In addition, the correlation between the depth (or the external water pressure) and the internal pressure of the dynamic buoyancy compensator can be recorded for controlling the propelling thereby sending the profiler to a predetermined depth.

The variable buoyancy profilers shown at FIG. 8 and FIG. 10 have the dynamic buoyancy compensators built as passive devices because water is moved in and out due to the difference of pressure inside and outside of the dynamic buoyancy compensator caused by the depth change when the profiler is moved vertically by the propeller. When the profiler needs to be moved to another target depth, the control board opens an electrical valve to expose the compenstor to the external water pressure. The propeller begins to move the profiler in a chosen direction. Through the open valve, water moves in or out equalizing pressure inside and outside. At the new target depth, the control board closes the electrical valve and stops the propeller. When the electrical valve is closed, the profiler maintains an equilibrium position at the new target depth.

The main property of the dynamic buoyancy compensator also allows to actively control the depth of the profiler using an internal pressure of the dynamic buoyancy compensator. The pressure inside of the dynamic buoyancy compensator responds approximate linearly to the amount of water pumped in, which allows the profiler to achieve the target depth by pumping known volume of water into dynamic buoyancy compensator. After the pumping is stopped, the profiler moves to the appropriate depth without multiple cycles of pumping as in the prior art.

In addition, the correlation between the depth and the corresponding water volume (or the internal pressure of the dynamic buoyancy compensator) can be recorded for controlling the water pumping thereby sending the profiler to a predetermined depth.

The variable buoyancy profilers shown at the FIG. 5, FIG. 7, FIG. 9, FIG. 11 have the dynamic buoyancy compensators built as active devices because water is pumping in and out of the dynamic buoyancy compensator by a reversible water pump. The variable buoyancy profiler according to FIG. 5 has the water filter 57 for cleaning input water so as to extend the lifetime of the valves and the water pump. Periodically, the water filter 57 should be replaced and the water pumping system should be cleaned and flushed to remove any mineral deposits or sediments.

Figure 5:
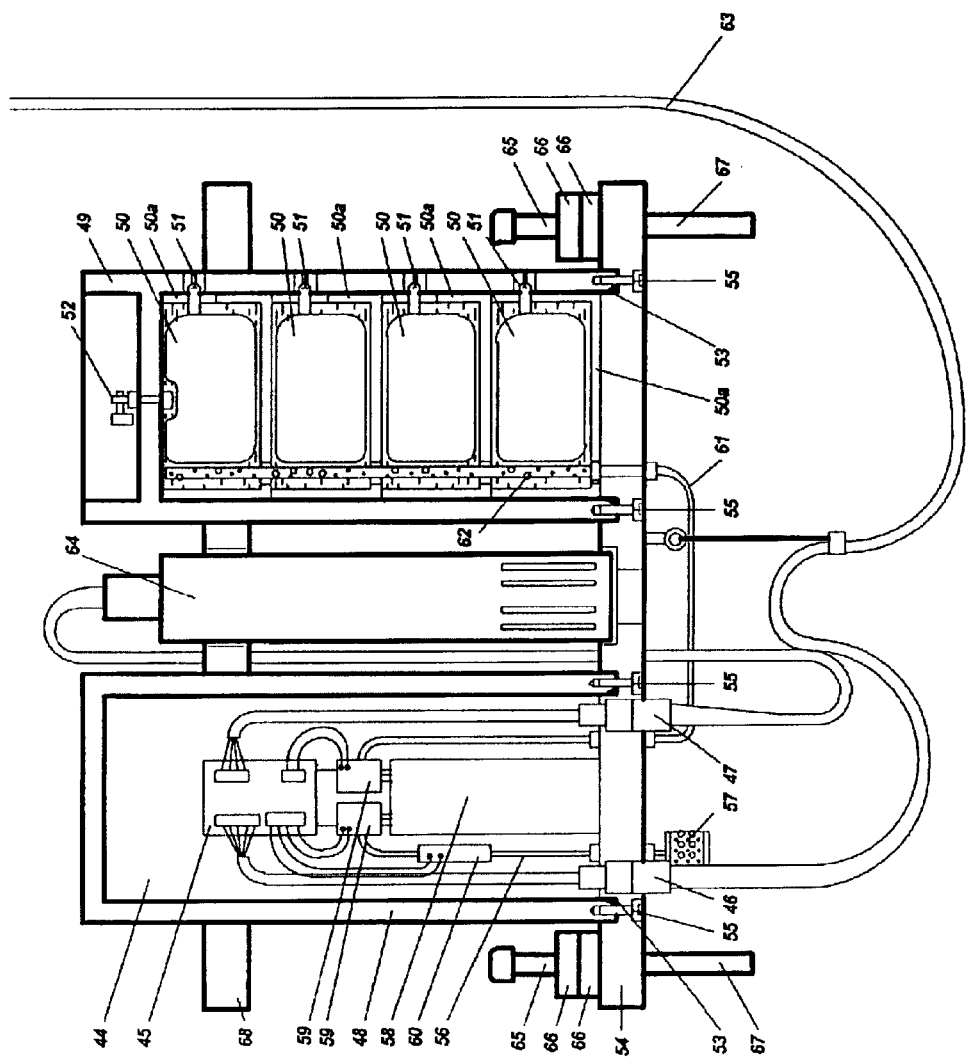
FIG. 5 is a schematic drawing of the variable buoyancy profiler.

The variable buoyancy profiler according to FIG. 7 has a closed water pumping system to increase time of operation without maintenance service. The dynamic buoyancy compensator made at the sealed part of protective cylinder 74. The protective cylinder filled with water is covered with the top plate 80 and sealed with the O-Ring 78. There is a rubber chamber 75 inside of the sealed compartment. In some embodiments, the dynamic buoyancy compensator may be more than one as shown in FIG. 5. To change the buoyancy of the profiler, the water pump 84 pumps water in or out of the rubber chamber 83. The rubber chamber 83 and the sealed compartment of the dynamic buoyancy compensator are filled with a special water solution, such as distilled water or water with chemical additives, to eliminate the formation of any deposits inside of the water pumping system including the valve orifices and the pump. The cylindrical surface of unsealed compartment 88 has multiple perforations to provide easy movement of water outside of the rubber chamber 83 via pumping operation. The compartment 88 is unsealed because water has almost zero compressibility and when pump press water in or out of the rubber chamber 83, the equal amount of water has to be moved in or out the unsealed compartment 88. The water moving in and out of the unsealed compartment 88 through multiple perforations could have sediments, but the water pumping with the pump 84 always clean. To further extend the operation time (without intermediate service) the cylindrical surface of unsealed compartment 88 is covered with or composed of a stainless steel mesh.

The variable buoyancy profiler according to the FIG. 11 has a depth sensor 22 to measure the outside pressure of water and a pressure sensor 222 to measure the pressure inside of the dynamic buoyancy compensator. The advantage of such an embodiment is the ability to work with any kind of sensing devices 216 even if they have no embedded depth sensor. It is another advantage in using the additional pressure sensor 222. The readings of the pressure sensor 222 are used as reference points during transition from one depth to another. At the time of deployment, water should be pumped to move the profiler in several steps beginning from the water surface to the maximum depth. At each depth, the profiler should stay until it comes to a stable position so as to take the pressure readings of the depth sensor 221 and the pressure sensor 222. The data is used to build a calibration curve for the depth as a function of the inside pressure of the dynamic buoyancy compensator. The calibration curve allows for the acquisition of the target depth by pumping the water in or out of the dynamic buoyancy compensator until the pressure inside is equal to the predetermined value, which corresponds to the target depth. After that valves near the pump should be closed. The profiler begins to move to the target depth and stops at a new equilibrium position. The advantage of such a mode of operation is less power consumption comparing with balancing the internal and external water pressure via multiple procedures of pumping water in and out near each target point.

Via the above-mentioned passively-controlling or actively-controlling methods, the invention achieves higher positioning accuracy by referencing a predetermined pressure inside of the dynamic buoyancy compensator to control the profiler movement via a propeller or a water pump. The pressure inside of the dynamic buoyancy compensator is used to control the propelling or the pumping in both methods. The external water pressure is used to check what pressure inside the dynamic buoyancy compensator should be at a predetermined depth in the passively-controlling method. The evaluation of predetermined pressures for subsequent profile uses data of current profile and improves accuracy.

A dynamic buoyancy compensator for each of these methods has a maximum buoyancy when the profiler is set on the water surface and a minimum buoyancy the profiler is set at the maximum depth. The actual buoyancy varies in different embodiments as discussed later.

In one embodiment, the profiler is connected to one end of the underwater cable, and another end of the cable is connected to the deployment platform or a buoy (FIG. 2). When the profiler is set near the water surface, the underwater cable is hung from the deployment platform. Half of the cable's negative buoyancy is preferably compensated by the positive buoyancy of the profiler via the dynamic buoyancy compensator therein. By varying the buoyancy of the profiler via dynamic buoyancy compensator to zero, the profiler is brought to the maximum depth.

Figure 12A:
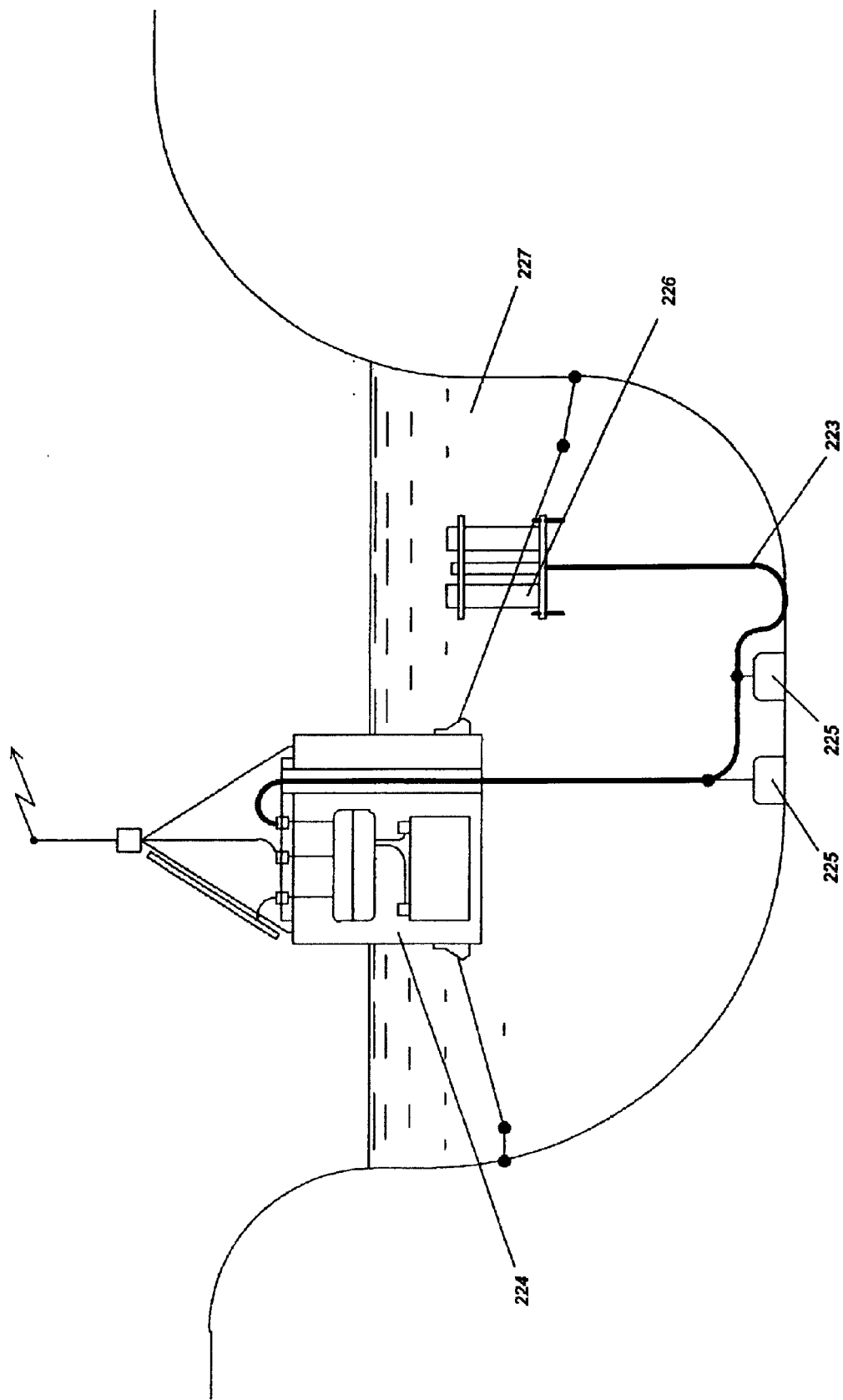
FIG. 12A is a schematic drawing of the remote sample station according to the invention with an underwater cable with negative buoyancy and intermediate anchors.

In another embodiment, the underwater cable 223 connected to the deployment platform 224 and has an intermediate anchors 225 as shown in FIG. 12A and the profiler 226 is floating in the body of water 227. When profiler is set near the water surface, it has maximum positive buoyancy which compensates the negative buoyancy of the full length of underwater cable. By varying the buoyancy of the profiler via the dynamic buoyancy compensator from maximum value to zero, the profiler is brought to the maximum depth.

Figure 12B:
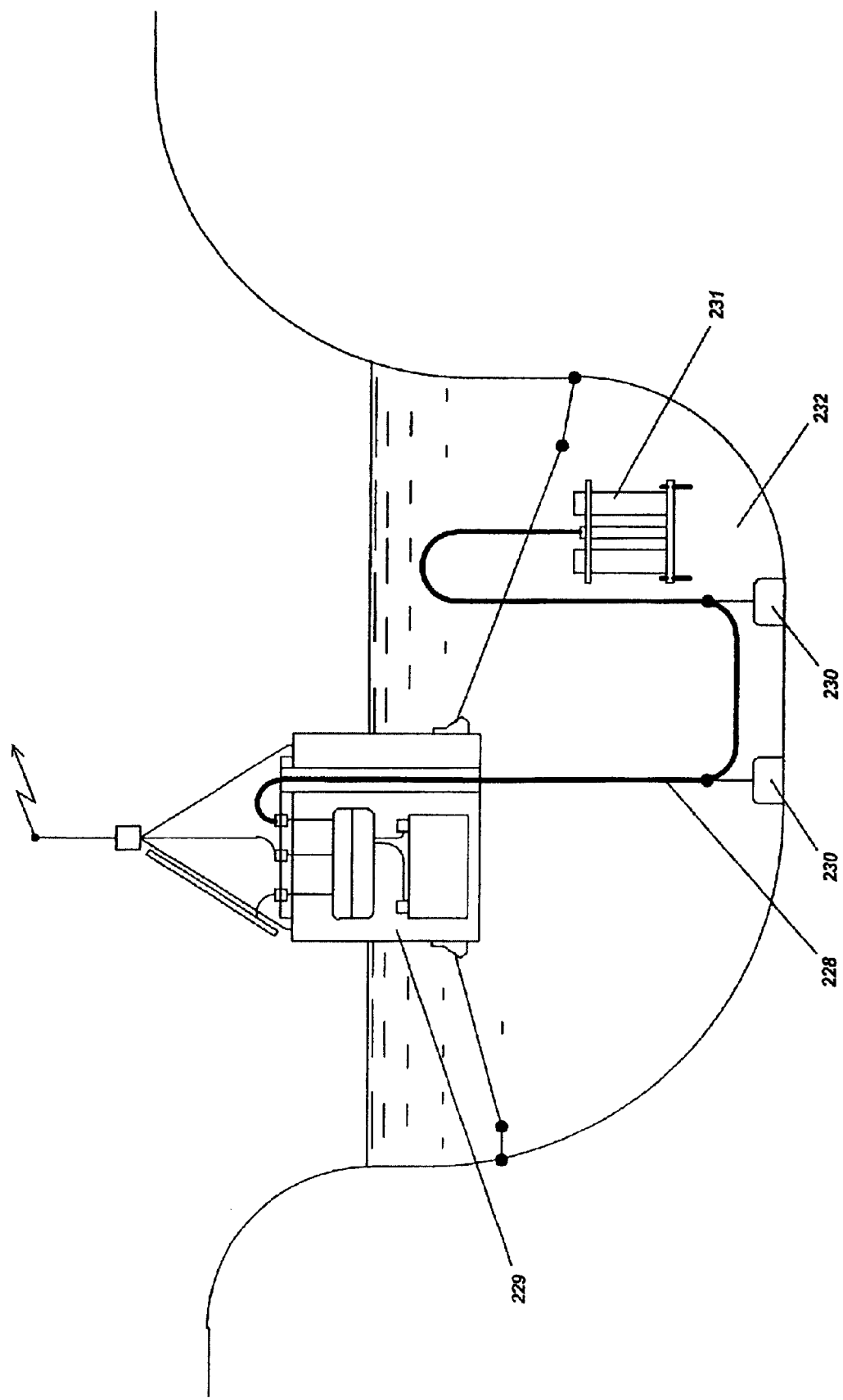
FIG. 12B is a schematic drawing of the remote sample station according to the invention with an underwater cable with positive buoyancy and intermediate anchors.

Some embodiments work with an underwater cable with positive buoyancy (FIG. 12B). Such an underwater cable 228 which is connected to the deployment platform 229 has intermediate anchors 230, and the profiler 231 is floating in the body of water 232. When the profiler is set near the water surface, it should have maximum buoyancy close to zero. By varying the buoyancy of the profiler via the dynamic buoyancy compensator from zero to negative buoyancy one half of the cable positive buoyancy, the profiler is brought to the maximum depth.

The controller unit located inside the buoy receives, processes, and stores data at selected intervals. Data is remotely downloaded when the base station contacts the unit or, if selected, when the unit contacts the base station. Data from meteorological sensors (air temperature, wind speed and direction, and barometric pressure), positioning device (GPS) and power cell condition (voltage) is also acquired and stored by the controller unit. One or multiple solar panels charge one or multiple battery units.

In short, the air inside the chamber of the prior art buoyancy profiler is not separated from the pumped water, but the air inside the rubber chambers of the invention is separated from the water during pumping by the rubber chambers. In addition, the water is pumped in and out of a volume between an inner wall of the rigid sealed compartment and an outer surface of the sealed elastic chamber/piston/sylphon of the invention. The invention further provides three methods for controlling a depth of the variable buoyancy profiler in a body of water: a) Moving the profiler to a target depth with an external force and connecting its dynamic buoyancy compensator to the body of water, and then disconnecting it from the body of water and turn off any external force. b) Moving the profiler to a target depth by pumping water into its dynamic buoyancy compensator which is connected to the body of water, and using a pressure inside of the dynamic buoyancy compensator and a pressure outside of the dynamic buoyancy compensator to check what pressure inside should be at the predetermined depth. This method utilizes the data of current profile to perform or evaluate a predetermined pressure for the next profile so as to improve an accuracy. c) Moving the profiler to a target depth, pumping water in its dynamic buoyancy compensator which is connected to the body of water, and using a predetermined pressure (obtained via Method b)) inside of the dynamic buoyancy compensator as a signal to stop pumping. This method allows to reach the target depth in one move. In contrast, the prior art method only pumps water in or out, then measures a depth to stop pumping, which takes several pumping and waiting periods. Such a system is unstable and oscillates near the target point. As a result, the prior art method consume more power consumption.

The principles, preferred embodiments and modes of operation of the present invention have been described in the foregoing specification. However, the invention which is intended to be protected is not limited to the particular embodiments disclosed. The embodiments described herein are illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A remote sampling system, comprising:
   at least one base station with A computer and at least one telecommunication device; and
   at least one autonomous sampling station having a deployment platform, a power supply, a controller unit and A communication system, a variable buoyancy profiler with at least one sensing device, and an underwater cable connected between the deployment platform and the profiler,
   wherein said variable buoyancy profiler has at least one sealed compartment with a control circuit, a water pumping system, an electrical connector for connecting to the underwater cable and one connector for each of said sensing device, and dynamic buoyancy compensator having at least one sealed rigid compartment connected to the water pumping system and at least one sealed rubber chamber containing air.

2. The system according to claim 1, wherein said communication system includes at least one of a cellular modem, a radio modem, a radio bridge to a separate landline modem, a satellite, and a fixed or networked communication system.

3. The system according to claim 1, wherein the sensing device includes at least one of a depth sensor and a pressure sensor.

4. The system according to claim 1, wherein said sensing device includes at least one of a depth sensor and a pressure sensor connected to the dynamic buoyancy compensator.

5. The system according to claim 1, wherein said sealed rubber chamber is pressurized to a different internal pressure therein such that a pressure response therein is close to linear to water has been pumped in.

6. The system according to claim 1, wherein said variable buoyancy profiler has a base plate having at least one cylindrical groove each with an O-Ring inside, and at least one cylinder each with a close end and an open end which is fitted in the groove and sealed by the O-ring respectively to provide an internal chamber therein, and several coil-type thread inserts therein said cylinders pulled to said base plate with screws.

7. The system according to claim 6, wherein the base plate has two cylindrical grooves and two cylinders, one of the cylinders accommendates said sealed compartment with a control circuit and the other of the cylinders accommendates the dynamic buoyancy compensator.

8. The system according to claim 1, wherein said water pumping system includes input water tubing connected to surrounding water through a water filter, a reversible water pump, at least one electrical valve, and output water tubing connected to said sealed compartment, said control circuit is connected with the water pump and the electrical valve to control pumping the surrounding water in or out of the variable buoyancy profiler.

9. The system according to claim 8, wherein said control circuit includes at least one adjustable voltage reference for stabilizing a pump current and thereof a maximum output pressure at a predetermined depth, and a semiconductor switch for changing a direction of the pump current.

10. The system according to claim 8, wherein said control circuit includes at least one modulated voltage reference for periodically changing a pump current and thereof a maximum output pressure.

11. The system according to claim 8, wherein said control circuit uses a voltage output from a flow meter as a voltage reference to stabilize a water flow from the pump.

12. The system according to claim 11, wherein the flow meter includes a differential pressure sensor connected to one section of the input or output tubing.

13. The system according to claim 7, wherein the cylinder accommodating the dynamic buoyancy compensator has a two way valve on the top of the cylinder.

14. The system according to claim 6, wherein said base plate has at least one weight holder for adjusting an initial buoyancy of said profiler.

15. The system according to claim 1, wherein said dynamic buoyancy compensator further including at least one unsealed compartment each with one sealed rubber chamber connected to said water pumping system so as to be pumped in or out with water.

16. The system according to claim 1, wherein said variable buoyancy profiler has at least one dynamic buoyancy compensator made as a cylinder with a sealed piston to be moved therein and an adjustable spring inserted between a bottom plate of the cylinder and said piston.

17. The system according to claim 16, wherein said piston is sealed with at least one O-Ring.

18. The system according to claim 1, wherein said variable buoyancy profiler has at least one sealed compartment with a control circuit, an electrical connector for underwater cable, one connector for each of said sensing device, and at least one sealed deformable compartment located within said sealed compartment for providing a maximum buoyancy when the profiler is set at a water surface and a minimum buoyancy when the profiler is set at a maximum depth.

19. The system according to claim 18, wherein said deformable compartment is provided by at least one sylphon with a spring operating therein.

20. The system according to claim 1, wherein said variable buoyancy profiler has at least one sealed compartment with a control circuit, a water controlling system, at least one electrical motor connected to said control circuit and a propeller for vertically moving the profiler in a body of water, an electrical connector for connecting to an underwater cable, one connector for each of said sensing device, and at least one sealed compartment connected to said water controlling system, wherein said sealed compartment has one of:

(1) at least one sealed rubber chambers containing air.

(2) a sealed piston to be moved therein and a adjustable spring inserted between a bottom plate of said sealed compartment and said piston.

(3) at least one sealed deformable compartment located within said sealed compartment for providing a maximum buoyancy when the profiler is set at a water surface and a minimum buoyancy when the profiler is set at a maximum depth.

21. The system according to claim 20, wherein said water controlling system includes input water tubing connected to surrounding water through a water filter and at least one electrical valve, and output water tubing connected to said sealed compartment therein, and the control circuit is connected to the electrical valve to control the electrical valve.

22. The system according to claim 21, wherein said water controlling system further includes a reversible water pump.

23. The system according to claim 20, wherein said sealed rubber chamber is pressurized to a different internal pressure therein such that a pressure response therein is close to linear to water has been pumped in.

24. The system according to claim 1, wherein said controller unit is directly connected with said sensing device.

25. The system according to claim 24, wherein said sensing device includes at least one of a geo positioning sensor (GPS), a radiation sensor, a photoactive radiation sensor (PAR), a meteorological sensor, a water temperature sensor, and a temperature sensing array.

26. A dynamic buoyancy compensator responding approximately linear to a water pressure created by an external water body, comprising at least one sealed rigid compartment with one sealed elastic chamber having a valve and containing pressurized air therein, wherein said sealed rigid compartment is connected to each other, and a volume between an inner wall of said rigid compartment and an outer surface of said sealed elastic chamber is filled with water and connected to the external water body through at least one electrical valve.

27. The dynamic buoyancy compensator according to claim 26, further comprising a pressure sensor connected to said sealed compartment so as to output a signal indicating a pressure inside said sealed compartment.

28. The dynamic buoyancy compensator according to claim 26, wherein said electrical valve is controlled by an external control unit.

29. The dynamic buoyancy compensator according to claim 26, further comprising at least one sylphon having a spring member therein, wherein a volume between an inner wall of said sealed rigid compartment and an outer surface of said sylphon is filled with water and connected to water body through at least one electrical valve.

30. The dynamic buoyancy compensator according to claim 29, further comprising a pressure sensor connected to said sealed rigid compartment so as to output a signal indicating a pressure inside said sealed rigid compartment.

31. The dynamic buoyancy compensator according to claim 29, wherein said electrical valve is controlled by an external control unit.

32. The dynamic buoyancy compensator according to claim 26, further comprising a piston moving therein and being urged by a spring member, wherein a volume between an inner wall of said sealed rigid compartment and an outer surface of said piston is filled with water and connected to the external water body through at least one electrical valve.

33. The dynamic buoyancy compensator according to claim 32, further comprising a pressure sensor connected to said sealed rigid compartment so as to output a signal indicating a pressure inside said sealed rigid compartment.

34. The dynamic buoyancy compensator according to claim 32, wherein said electrical valve is controlled by an external control unit.

35. A method for controlling a depth of a variable buoyancy profiler in a body of water comprising the steps of:

attaching the variable buoyancy profiler with a dynamic buoyancy compensator responding approximately linear to an external pressure created by the body of water;

connecting the dynamic buoyancy compensator to the body of water to receive the external pressure therefrom;

moving the profiler to the depth with an external force;

maintaining the profiler at the depth for a period of time to equalize an internal pressure of the dynamic buoyancy compensator with the external pressure at the depth;

terminating the external force; and isolating the dynamic buoyancy compensator from the body of water to disconnect the external pressure.

36. The method according to claim 35, wherein the dynamic buoyancy compensator provides at the surface a maximum buoyancy when the profiler is set at a surface of the body of water and a minimum buoyancy when the profiler is set at the maximum depth in the body of water.

37. The method according to claim 35, wherein the external force is provided via a propeller drive.

38. The method according to claim 35, further comprising connecting an underwater cable with buoyancy between the profiler and a floating buoy set on a surface of the body of water, and varying the internal pressure of the dynamic buoyancy compensator thereby adjusting the buoyancy of the profiler against the buoyancy of the underwater cable so as to control the depth of the profiler.

39. The method according to claim 38, wherein the buoyancy of the profiler is positive and set to be equal to half of the buoyancy of the underwater cable which is negative and varies to zero to bring the profiler to the maximum depth.

40. The method according to claim 38, further comprising attaching an anchoring device to the underwater cable to cancel out buoyancy of the floating buoy, wherein the buoyancy of the profiler is positive and set to be equal to the buoyancy of the underwater cable which is negative and varies to zero to bring the profiler to the maximum depth.

41. The method according to claim 38, further comprising attaching an anchoring device to the underwater cable to cancel out buoyancy of the floating buoy, wherein the buoyancy of the profiler is zero and set to be negative and equal to half of the buoyancy of the underwater cable which is positive to bring the profiler to the maximum depth.

42. A method for controlling a depth of a variable buoyancy profiler in a body of water comprising the steps of:

attaching the variable buoyancy profiler with a dynamic buoyancy compensator responding approximately linear to an external pressure created by the body of water;

connecting the dynamic buoyancy compensator to the body of water to receive the external pressure therefrom;

pumping water inside or outside of the buoyancy compensator to equalize an internal pressure of the dynamic buoyancy compensator with a predetermined pressure or the external pressure at the depth; and disconnecting the dynamic buoyancy compensator from the body of water to insulate the external pressure.

43. The method according to claim 42, the dynamic buoyancy compensator provides at the surface a maximum buoyancy when the profiler is set at a surface of the body of water and a minimum buoyancy when the profiler is set at the maximum depth in the body of water.

44. The method according to claim 42, wherein the pumping is conducted via a pump.

45. The method according to claim 42, further comprising connecting an underwater cable with buoyancy between the profiler and a floating buoy set on a surface of the body of water, and varying the internal pressure of the dynamic buoyancy compensator thereby adjusting the buoyancy of the profiler against the buoyancy of the underwater cable so as to control the depth of the profiler.

46. The method according to claim 45, wherein the buoyancy of the profiler is positive and set to be equal to half of the buoyancy of the underwater cable which is negative and varies to zero to bring the profiler to the maximum depth.

47. The method according to claim 45, further comprising attaching an anchoring device to the underwater cable to cancel out buoyancy of the floating buoy, wherein the buoyancy of the profiler is positive and set to be equal to the buoyancy of the underwater cable which is negative and varies to zero to bring the profiler to the maximum depth.

48. The method according to claim 45, further comprising attaching an anchoring device to the underwater cable to cancel out buoyancy of the floating buoy, wherein the buoyancy of the profiler is zero and set to be negative and equal to half of the buoyancy of the underwater cable which is positive to bring the profiler to the maximum depth.

49. The method according to claim 42, further comprising collating the depth with a volume of the pumped water the thereby sending the profiler to the depth subsequently by pumping the volume of water therein.

* * * * *